United States Patent [19]

Gavin et al.

[11] 4,183,816

[45] Jan. 15, 1980

[54] USE OF 2,4-DI(LOWER ALKYL)-1,2,4-THIADIAZOLIDIN-3,5-DIONES AS ADDITIVES FOR FUNCTIONAL FLUIDS

[75] Inventors: David F. Gavin, Cheshire; Frank J. Milnes, Guilford; John R. Parziale, Wallingford, all of Conn.

[73] Assignee: Olin Corporation, New Haven, Conn.

[21] Appl. No.: 956,555

[22] Filed: Nov. 1, 1978

[51] Int. Cl.$^2$ .................... C10M 1/20; C10M 1/32; C10M 1/38
[52] U.S. Cl. ................... 252/47.5; 252/78.1; 548/129
[58] Field of Search ............ 252/47.5, 78.1; 260/302 D, 302 SD

[56] References Cited

U.S. PATENT DOCUMENTS

| | | | |
|---|---|---|---|
| 3,374,240 | 3/1968 | Ottmann et al. | 260/306.7 |
| 3,900,485 | 8/1978 | Krenzer | 260/302 D |
| 3,980,573 | 9/1976 | Okorodudu | 260/302 SD |

*Primary Examiner*—Patrick Garvin
*Assistant Examiner*—J. V. Howard
*Attorney, Agent, or Firm*—William A. Simons; T. P. O'Day

[57] ABSTRACT

Disclosed is the use of 2,4-di(lower alkyl)-1,2,4-thiadiazolidin-3,5-diones as ashless load-carrying additives for functional fluids. These thiadiazolidin-3,5-diones have the formula:

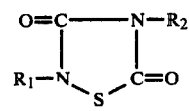

wherein $R_1$ and $R_2$ are lower alkyl groups having 1–4 carbon atoms.

7 Claims, No Drawings

USE OF 2,4-DI(LOWER ALKYL)-1,2,4-THIADIAZOLIDIN-3,5-DIONES AS ADDITIVES FOR FUNCTIONAL FLUIDS

BACKGROUND OF THE INVENTION

1. Field of the Invention

The present invention relates to the use of 2,4-di(-lower alkyl)-1,2,4-thiadiazolidin-3,5-dione compounds as load-carrying additives for functional fluids such as lubricants and hydraulic fluids.

2. Description of the Prior Art

The employment of chemical additives in lubricants, hydraulic oils and similar functional fluids to improve the overall load-carrying characteristics of the fluid is well known. Probably, the most commonly employed load-carrying additives are the zinc dialkyl and diaryl dithiophosphates. However, for many applications it is necessary to employ ashless formulations (i.e., formulations that leave substantially no ash residue upon evaporation or combustion). In such instances, these zinc-containing compounds are not satisfactory.

Many load-carrying additives have, alternatively, been found which have this desired ashless characteristic. However, there is still a need in the art to find more suitable ashless additives. To meet that need is the primary object of this invention.

The 2,4-di(lower alkyl)-1,2,4-thiadiazolidin-3,5-diones of the present invention have been employed as agricultural chemicals such as foliar and soil fungicides. See U.S. Pat. No. 3,374,240 which issued to Ottman and Hooks, Jr. on Mar. 19, 1968. However, this reference does not teach or suggest the present inventive use.

BRIEF SUMMARY OF THE INVENTION

The present invention, therefore, is directed to the use of 2,4-di(lower alkyl)-1,2,4-thiadiazolidin-3,5-dione compounds as additives for functional fluids, said thiadiazolidin-3,5-diones having the formula:

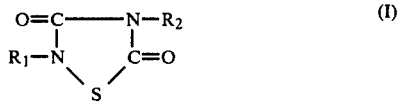

(I)

wherein $R_1$ and $R_2$ are lower alkyl groups having 1-4 carbon atoms.

These additives improve the load-carrying characteristics of functional fluids while being ashless in nature.

DETAILED DESCRIPTION

The 2,4-di(lower alkyl)-1,2,4-thiadiazolidin-3,5-dione compounds of the present invention may be prepared form the corresponding S-chloroisothiocarbonyl chloride and corresponding isocyanates according to the method disclosed in U.S. Pat. No. 3,374,240, which issued to Ottman and Hooks, Jr. on May 19, 1968. This patent is incorporated herein by reference in its entirety. Alternatively, the additives of the present invention may be made by the same general method disclosed in the Ottman and Hooks, Jr. patent except using an isothiocyanate (with a chlorinating agent) instead of an S-chloro isothiocarbamyl chloride. See Example 1, below. Furthermore, these thiadiazolidin-3,5-dione compounds, may of course, be synthesized by other conventional methods and the present invention is not intended to be limited to any particular method of making the compound. Regardless the method of synthesis, the desired compound may be recovered from the reaction mixture by any conventional recovery method, including filtration, extraction and recrystallization techniques.

The preferred compound of the class of Formula (I) is 2,4-dimethyl-1,2,4-thiadiazolidin-3,5-dione because of its ease of preparation and its slightly better load-carrying characteristics.

As previously indicated, the compounds of the present invention are substantially ashless in nature. For purposes of this invention, an ashless additive is one which shows substantially no ash when tested according to the procedure set forth in ANSI/ASTM D482-74.

It is generally considered by those skilled in the art that load-carrying additives may be divided into two classes, namely, antiwear and extreme pressure additives. When two lubricated moving surfaces are lightly loaded against each other, they are separated by an elasto-hydrodynamic oil film; as the load increases so the oil film thickness decreases. When the oil film thickness approaches the dimensions of the surface roughness, it will be penetrated by surface asperities. It is in this region that antiwear additives function by improving the oil film strength and reducing intermetallic contact.

As the load is increased further, the bulk oil film collapses and mere antiwear additives are no longer sufficient to protect the surface. In this latter region, extreme pressure (EP) additives function by reacting with the metal surface to form a compound which prevents or delays welding of the metal surfaces.

For purposes of this invention, the relative antiwear characteristics of functional fluids containing additives are determined by the test procedure set forth in ANSI/ASTM D-2266-67 (Reapproved 1977)—WEAR PREVENTIVE CHARACTERISTICS OF LUBRICATING GREASE (FOUR-BALL METHOD). Still further, for purposes of this invention, the extreme pressure properties of functional fluids containing additives are determined by the test procedure set forth in ANSI/ASTM D-2783-71 (Reapproved 1976)—MEASUREMENT OF EXTREME-PRESSURE PROPERTIES OF LUBRICATING FLUIDS (FOUR-BALL METHOD).

As functional fluid additives, the present compounds normally comprise a minor proportion by weight of the total functional fluid, with a base stock fluid normally comprising a major proportion by weight of total functional fluid. Preferably, the instant additives comprise from about 0.01% to about 10%, more preferably, from about 0.1% to about 5% by weight of the total functional fluid. These weight percents are based on the filtered functional fluid in the absence of any diluents or solvents.

Any conventional method of formulating functional fluids to employ the present additives may be used and it is not intended to limit this invention to any particular method of formulation. The additives of the present invention are particularly suitable for incorporating in functional fluids such as lubricating oil compositions and hydraulic fluid compositions.

Lubricating oil compositions include crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants and other lubricating oil and grease compositions may also benefit from the incorporation therein of the additive compositions of this invention.

Hydraulic fluid compositions contemplated by the present invention include hydraulic brake fluids, hydraulic steering fluids, fluids used in hydraulic lifts and jacks. Also included in the scope of this invention are hydraulic fluids used in hydraulic systems such as employed in heavy equipment and transportation vehicles including highway and construction equipment, railways, planes and aquatic vehicles.

The base fluids of such lubricating oil compositions and hydraulic fluid compositions may be composed of either natural or synthetic lubricating oils or mixtures thereof. In particular, natural lubricating oils contemplated for this invention include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propyleneisobutylene copolymers, chlorinated polybutylenes); poly(1-hexanes), poly(1-octanes), poly(1-decene), and mixtures thereof; alkylbenzenes (e.g., dodecylbenzenes, tetradecylbenzenes, dinonylbenzenes, di-(2-ethylhexyl)-benzenes,); polyphenyls (e.g., biphenyls, terphenyls, alkylated polyphenyls,); alkylated diphenyl ethers and alkylated diphenyl sulfides and the derivatives, analogs and homologs thereof and the like.

Alkylene oxide homopolymers and interpolymers and derivatives thereof where the terminal hydroxyl groups have been modified by esterification, etherification, constitute another class of known synthetic lubricating oils. These are exemplified by the oils prepared through polymerization of ethylene oxide or propylene oxide, the alkyl and aryl ethers of these polyoxyalkylene polymers (e.g., diphenyl ether of polyethylene glycol having a molecular weight of 500–1,000 diethyl ether of polypropylene glycol having a molecular weight of 1,000–1,500), or mono- and polycarboxylic esters of said polyethylene glycol, for example, the acetic acid esters, mixed $C_3$–$C_8$ fatty acid esters, or the $C_{13}$Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids,) with a variety of alcohols (e.g., butyl alcohol, hexy alcohol, dodecyl alcohol, 2-ethylhexyl alcohol, ethylene glycol, diethylene glycol monoether, propylene glycol. Specific examples of these esters include dibutyl adipate, di(2-ethylhexyl)sebacate, di-n-hexyl fumarate, dioctyl sebacate, diisooctyl azelate, diiodecyl azelate, didioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers wuch as neopentyl glycol, trimethylol propane, pentaerythritol, dipentaerythritol, tripentaerythritol, and the like.

Silicon-based oils such as the polyalkylpolyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid), polymeric tetrahydrofurans and the like.

Unrefined, refined and rerefined oils, either natural or synthetic (as well as mixtures of two or more of any of these) of the type disclosed hereinabove may be used as the base stock of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill of the art such as solvent extraction, secondary distillation, acid or base extraction, filtration, percolation, etc. Rerefined oils are obtained by processes, similar to those used to obtain refined oils, applied to refined oils which have been already used in service. Such rerefined oils are also known as reclaimed or reprocessed oils and often are additionally processed by techniques directed to removal of spent additives and oil breakdown products.

The compounds of Formula I of this invention may be used alone or in combination with other lubricant additives such as detergent, dispersants, pour-point depressing agents, antifoam agents, viscosity modifiers, other extreme pressure load-bearing agents, corrosion inhibitors, antiwear agents, antioxidants, and the like.

These additional additives are well known in the art and a brief survey of conventional additives for lubricating compositions is contained in the publications, LUBRICANT ADDITIVES, C. V., Smalheer and R. Kennedy Smith, published by Lezius-Hiles Co., Cleveland, Ohio, 1967 and LUBRICANT ADDITIVES, M. W. Ranney, published by Noves Data Corp., Park Ridge, N.J., 1973, which are herein incorporated by reference in their entirety.

The ash-containing detergents are well known neutral and basic alkali or alkaline earth metal salts of sulfonic acids, carboxylic acids or organophosphorus-containing acids. These phosphorus-containing acids are characterized by at least one direct carbon-to-phosphorus linkage, and can be prepared by steam-treating an olefin polymer, i.e., polyisobutylene, with a phosphorizing agent such as phosphorus trichloride, phosphorus heptasulfide, phosphorus pentasulfide, phosphorus trichloride and sulfur, white phosphorus and a sulfur halide, or phosphorothioic chloride. When used as an ash-containing detergent, the most commonly used salts of these acids are the sodium, potassium, lithium, calcium, magnesium, strontium, and barium salts. The calcium and barium salts are used more extensively than the others. The "basic salts" are those metal salts known in the art wherein the metal is present in a stoichiometrically larger amount than that necessary to neutralize the acid. The calcium and the barium overbased petrosulfonic acids are typical examples of such basic salts. The ashless dispersants are also a well known class of materials used as additives for lubricating oils and fuels. They are particularly effective as dispersants at low temperatures. The hydrocarbon-substituted succinic acids and their derivatives can be used as stabilizing agents in the preparation of the lubricant compositions of this invention and are representative of the dispersants. These dispersants include products obtained by the reaction of the $C_{30}$ or greater hydrocarbon-substituted succinic acid compounds and alkylene polyamines or polyhydric alcohols, which can be further post-treated with materials such as boric acids or metal compounds.

Pour point depressing agents are illustrated by the polymers of ethylene, propylene, isobutylene, and poly-(alkylmethacrylates). Anti-foam agents include polymeric alkyl siloxanes, poly-(alkyl methacrylates), copolymers of diacetone acrylamide and alkyl acrylates or methacrylates, and the condensation products of alkyl phenol with formaldehyde and an amine. Viscosity index improvers include, polymerized and copolymerized alkyl methacrylates and polyisobutylenes.

Other extreme pressure agents, corrosion-inhibiting agents, and oxidation-inhibiting agents are exemplified by chlorinated aliphatic hydrocarbons, such as chlorinated wax; organic sulfides and polysulfides; such as benzyl disulfide, bis-(chlorobenzyl)disulfide, dibutyl tetrasulfide, sulfurized sperm oil, sulfurized methyl ester of oleic acid, sulfurized alkyl phenol, sulfurized dipentene, sulfurized terpene, and sulfurized Diels-Alder adducts; phosphosulfurized hydrocarbons, such as the reaction product of phosphorus sulfide with terpentine or methyl oleate; phosphorus esters such as the dihydrocarbon and trihydrocarbon phosphites, i.e., dibutyl phosphite, diheptyl phosphite, dichclohexyl phosphite, pentylphenyl phosphite, dipentyl phenyl phosphite, tridecyl phosphite, distearyl phosphite, and polypropylene substituted phenyl phosphite; metal thiocarbamates, such as zinc dioctyldithiocarbamate and barium heptylphenol dithiodicarbonate; Group II metal salts of phosphorordithioic acids, such as zinc dicyclohexyl phosphorodithioate, and the zinc salt of a phosphorodithioic acid.

The following examples are provided to further illustrate the present invention. All parts and proportions, unless otherwise explicitly indicated, are by weight.

EXAMPLE 1

Preparation of
2,4-dimethyl-1,2,4-thiadiazolidin-3,5-dione

Chlorine was passed into a cold (0° F. to −10° F.) stirred mixture of 36.5 g (0.5 mole) of methylisothiocyanate and 28.5 g (0.5 mole) of methylisocyanate until 35.5 g (0.5 mole) was absorbed. The resulting precipitate was collected by filtration and added portionwise with stirring to 300 ml of hot water, maintaining a temperature of 60°-70° C. A white, crystalline solid on developed standing overnight at room temperature, and additional solid was formed by concentration of the aqueous mixture in vacuo. The solids were collected by filtration and redissolved in hot water. The concentrated aqueous solution was neutralized with sodium bicarbonate to give a white crystalline product. Recrystallization from hexane yielded 54 1 g (74%) of material melting at 64°-65° C., and having the following elemental analysis.

Calculated for: $C_4H_6N_2SO_2$: C, 32.83; H, 4.14; N, 19.16. Found: C, 32.39; H, 4.14; N, 19.85.

EXAMPLE 2

Preparation of
2-n-butyl-4-methyl-1,2,4-thiadiazolidin-3,5-dione

A solution of 40 g (0.55 mole) of methylisothiocyanate and 63 g (0.64 mole) of butylisocyanate in 400 ml of chloroform was stirred at 0° F. to −10° F., while chlorine gas was passed through. When 42 g (0.6 mole) of chlorine had been absorbed, the mixture was diluted with an equal volume of hexane and the solids were collected by filtration. The solid adduct was added portionwise with stirring to 400 ml of cold water. The mixture was extracted with three 100 ml portions of ether. The organic extract was dried over sodium sulfate. The drying agent was then removed by filtration. The hexane and ether were evaporated to leave 60 g (60% yield) of water-white oil, having the following elemental analysis.

Calculated for: $C_7H_{12}N_2SO_2$: C, 44.47; H, 6.83; S, 16.96. Found: C, 44.47; H, 6.68; S, 15.97.

EXAMPLE 3

Preparation of
2,4-di-n-butyl-1,2,4-thiadiazolidin-3,5-dione

The preparation of this compound may be found in Example 1 of U.S. Pat. No. 3,374,240, mentioned above.

EXAMPLES 4–29

The additive compounds made in Examples 1–3 were formulated with various commercially available base fluids and such formulations were tested in a 4-ball tester apparatus according to test procedures set forth in ANSI/ASTM D-2266-67 and ANSI/ASTM D-2783-71 to determine the antiwear and extreme pressure characteristics, respectively, of the fluids.

Two grams of each additive compound were mixed with 196 grams of a base fluid and 2 grams of an antioxidant, phenyl alpha napthyl amine, at room temperature. The mixture was then heated and stirred (e.g., 100° F. to 250° F.) until the additive and anti-oxidant dissolved. The resulting solution was filtered to give a clear homogeneous fluid. Then, the solutions were tested in the 4-ball testers. The antiwear tests were conducted at 40 kg load weight, 1,800 rpm, and 167° F. The results of these tests are given in Tables I and II.

TABLE I

| | Four-Ball Antiwear Test | | |
|---|---|---|---|
| Ex. | Load-Carrying Additive | Base Fluid | Average Scar Diameter |
| 4 | none | SUNVIS 31[1] | .63 mm |
| 5 | 2,4-dimethyl- | SUNVIS 31[1] | .45 |
| 6 | 2-n-butyl-4-methyl- | SUNVIS 31[1] | .57 |
| 7 | 2,4-di-n-butyl- | SUNVIS 31[1] | .57 |
| 8 | none | POLY-G-WI-625[2] | .44 |
| 9 | 2,4-dimethyl- | POLY-G-WI-625[2] | .48 |
| 10 | 2-n-butyl-4-methyl- | POLY-G-WI-625[2] | .43 |
| 11 | 2,4-di-n-butyl- | POLY-G-WI-625[2] | .37 |
| 12 | none | PAO-10[3] | 2.24 |
| 13 | 2-n-butyl-4-methyl- | PAO-10[3] | 0.62 |
| 14 | none | MONOPLEX DOS[4] | 1.81 |
| 15 | 2,4-dimethyl- | MONOPLEX DOS[4] | 0.72 |
| 16 | 2-n-butyl-4-methyl- | MONOPLEX DOS[4] | 0.94 |

TABLE II

Four-Ball Extreme Pressure Test

| Example | Load-Carrying Additive | Base Fluid | Load Wear Index | Last Non-Seizure Load | Weld Load |
|---|---|---|---|---|---|
| 17 | none | SUNVIS 31[1] | 14 kg | 32 kg | 160 kg |
| 18 | 2,4-dimethyl- | SUNVIS 31[1] | 25 | 50 | 200 |
| 19 | 2-n-butyl-4-methyl- | SUNVIS 31[1] | 21 | 40 | 160 |
| 20 | 2,4-di-n-butyl- | SUNVIS 31[1] | 21 | 40 | 160 |
| 21 | none | POLY-G-WI-625[2] | 22 | 50 | 126 |
| 22 | 2,4-dimethyl- | POLY-G-WI-625[2] | 36 | 80 | 250 |
| 23 | 2-n-butyl-4-methyl- | POLY-G-WI-625[2] | 28 kg | 63 kg | 160 kg |
| 24 | 2,4-di-n-butyl- | POLY-G-WI-625[2] | 24 | 50 | 160 |
| 25 | none | PAO-10[3] | 17 | 40 | 160 |
| 26 | 2-n-butyl-4-methyl- | PAO-10[3] | 34 | 80 | 160 |
| 27 | none | MONOPLEX DOS[4] | 17 | 40 | 126 |
| 28 | 2,4-dimethyl- | MONOPLEX DOS[4] | 42 | 80 | 200 |
| 29 | 2-n-butyl-4-methyl- | MONOPLEX DOS[4] | 22 | 50 | 126 |

[1]SUNVIS 31 is a high viscosity index, neutral petroleum oil of paraffinic base and is commercially available from the Sun Oil Company.
[2]POLY-G-WI-625 is a monobutylether of approximately 1800 molecular weight polypropylene glycol and is commercially available from the Olin Corporation.
[3]PAO-10 is a high viscosity index polyalphaolefin of polymerized 1-decene and is commercially available from Uniroyal, Inc.
[4]MONOPLEX DOS is di-iso octyl sebacate and is commercially available from Rohm & Haas Co.

What is claimed is:

1. A functional fluid composition comprising a major amount of a base fluid selected from the group consisting of lubricants and hydraulic oils and minor amount of an additive selected from the group consisting of 2,4-di(lower alkyl)-1,2,4-thiadiazolidin-3,5-diones of the formula:

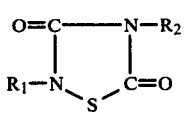

wherein $R_1$ and $R_2$ are lower alkyl groups having 1–4 carbon atoms.

2. The functional fluid composition of claim 1, wherein said functional fluid composition is a hydraulic fluid composition.

3. The functional fluid composition of claim 1, wherein said functional fluid composition is a lubricating oil composition.

4. The functional fluid composition of claim 1, wherein said additive is 2,4-dimethyl-1,2,4-thiadiazolidin-3,5-dione.

5. The functional fluid composition of claim 1, wherein said additive is 2-n-butyl-4-methyl-1,2,4-thiadiazolidin-3,5-dione.

6. The functional fluid composition of claim 1, wherein said additive is 2,4-di-n-butyl-1,2,4-thiadiazolidin-3,5-dione.

7. The functional fluid composition of claim 1, wherein said additive is present in an amount from about 0.01% to about 10% by weight of said functional fluid composition.

* * * * *